US008128941B2

(12) United States Patent
Lyashchenko et al.

(10) Patent No.: US 8,128,941 B2
(45) Date of Patent: Mar. 6, 2012

(54) ASSAY FOR DETECTING TUBERCULOSIS IN NONHUMAN PRIMATES

(75) Inventors: Konstantin Lyashchenko, East Setauket, NY (US); Javanbakhsh Esfandiari, Stonybrook, NY (US); Candace McCombs, Athens, GA (US)

(73) Assignee: Chembio Diagnostic Systems, Inc., Medford, NY (US)

( * ) Notice: Subject to any disclaimer, the term of this patent is extended or adjusted under 35 U.S.C. 154(b) by 1020 days.

(21) Appl. No.: 11/212,922

(22) Filed: Aug. 26, 2005

(65) Prior Publication Data

US 2006/0057621 A1    Mar. 16, 2006

Related U.S. Application Data

(60) Provisional application No. 60/605,304, filed on Aug. 26, 2004.

(51) Int. Cl.
*A61K 39/04* (2006.01)
*A61K 39/02* (2006.01)
*G01N 33/53* (2006.01)

(52) U.S. Cl. ............. 424/248.1; 424/130.1; 424/164.1; 424/168.1; 424/184.1; 424/234.1; 435/4; 435/7.1; 435/7.32

(58) Field of Classification Search ............. 424/130.1, 424/164.1, 168.1, 184.1, 234.1, 248.1; 435/4, 435/7.1, 7.32
See application file for complete search history.

(56) References Cited

U.S. PATENT DOCUMENTS

| | | | |
|---|---|---|---|
| 4,956,302 | A | 9/1990 | Gordon et al. |
| 6,841,159 | B2 | 1/2005 | Simonson |

OTHER PUBLICATIONS

Lyashchenko, K.P., et al. Journal of Immunological Methods, vol. 242, pp. 91-100, 2000.*
Harboe, M., et al. Scandinavian Journal of Immunology, vol. 55, pp. 82-87, 2002.*
Amadora, Massimo, et al., "Use of Recombinant Proteins in Antibody Tests for Bovine Tuberculosis," Veterinary Microbiology 85, (2002) 379-389.
Houghton, Raymond L., et al., "Use of Multiepitope Polyproteins in Serodiagnosis of Active Tuberculosis," Clinical and Diagnostic Laboratory Immunology, Jul. 2002, p. 883-891.
Kanaujia, G.V., et al., "Detection of Early Secretory Antigenic Target-Antibody for Diagnosis of Tuberculosis in Non-Human Primates", Comparative Medicine, 2003, vol. 53, No. 6, pp. 602-606.
Koo, Hye Cheong, et al., "Use of rMPB70 Protein and ESAT-6 Peptide as Antigens for Comparison of the Enzyme-Linked Immunosorbent, Immunochromatographic, and Latex Bead Agglutination Assays for Serodiagnosis of Bovine Tuberculosis," Journal of Clinical Microbiology, Sep. 2005, p. 4498-4506.
Lyashchenko, Konstantin P., et al., "Diversity of Antigen Recognition by Serum Antibodies in Experimental Bovine Tuberculosis," Infection and Immunity, Nov. 1998, p. 5344-5349.
Raja, Alamelu, et al., "Immunoglobulin G, A, and M Responses in Serum and Circulating Immune Complexes Elicited by the 16-Kilodalton Antigen of *Mycobacterium tuberculosis*," Clinical and Diagnostic Laboratory Immunology, Mar. 2002, p. 308-312.
Rolinck-Werninghaus, Claudia, et al., "The Potential of Recombinant Antigens ESAT-6, MPT63 and Mig for Specific Discrimination of *Mycobacterium tuberculosis* and *M. avium* Infection," Research Letter, 2003.
Waters, W. R., et al., "Antigen Recognition by Serum Antibodies in White-Tailed Deer (*Odocoileus virginianus*) Experimentally Infected with *Mycobacterium bovis*," Clinical Diagnostic Laboratory Immunology, Sep. 2004, p. 849-855.
Zengyi Chang, et al., "*Mycobacterium tuberculosis* 17-kDa Antigen (Hsp16.3) Functions as an Oligomeric Structure in Vitro to Suppress Thermal Aggregation," The Journal of Biological Chemistry, vol. 271, No. 12, Issue of Mar. 22, pp. 7218-7223, 1996.

* cited by examiner

*Primary Examiner* — Rodney P. Swartz
(74) *Attorney, Agent, or Firm* — Gordon & Jacobson, PC (57) ABSTRACT

Systems, methods, and compositions for a diagnostic method for detecting TB in non-human primates that is easy to use, sensitive, and specific. The method utilizes recombinant mycobacterial antigens, such as polyfusion proteins. The method utilizes an antigen-antibody-antigen arrangement to detect TB infection in nonhuman primates. The method can detect IgM antibodies to TB, in addition to IgG antibodies, providing ability to detect TB earlier in nonhuman primate TB infection as compared to conventional TB tests.

43 Claims, 2 Drawing Sheets

ASSAY FOR DETECTING TUBERCULOSIS IN NONHUMAN PRIMATES

This application claims the benefit of provisional patent application No. 60/605,304, filed on Aug. 26, 2004.

FIELD OF INVENTION

The present invention relates to methods and compositions for detecting the presence of mycobacterial organisms, and in particular to methods and compositions for rapidly detecting tuberculosis infections in nonhuman primates.

BACKGROUND

Tuberculosis (TB) is one of the most important bacterial diseases of nonhuman primates (Adams et al., *Biosafety in Nonhuman Primates in Biomedical Research: Biology and Management*, (eds) Bennett, B. T., Abee, C. R. and R. Henrickson, Academis Press, San Diego, 1995). This is particularly true for captive nonhuman primate colonies, in which close quarters among colony members allow this highly contagious disease to spread rapidly. As in humans, most reported cases of this disease are caused by the acid-fast bacillus *Mycobacterium tuberculosis* or *Mycobacterium bovis*. And because these organisms are communicable between nonhuman primates and humans, nonhuman primate TB also poses a serious public health threat to humans that come into contact with infected animal colonies (Adams et al., 1995; Kalter et al., *Develop. Boil. Standard* 41:85-91, 1978).

Although the same TB organisms infect nonhuman primates and humans, morbidity and mortality rates are higher among nonhuman primates. This difference primarily stems from the distinct clinical manifestations of TB exhibited in humans and nonhuman primates. In humans, about 90% of all infected subjects are able to suppress active TB through cell-mediated immunity into a dormant- or latent-state. During the latent state of TB infection, the ability to spread the disease to others is very low and clinical symptoms are not apparent or nonexistent. Unlike humans, however, nonhuman primates do not exhibit a latent state. Once a nonhuman primate is infected, it presents with the active form of the disease, which it can readily spread to colony members and humans. Sadly, any infected nonhuman primates must either be isolated from its colony and humans or destroyed.

Because of the problems associated with nonhuman primate TB, careful surveillance for TB infections is very important for the welfare and good management of all captive nonhuman primates. In an effort to prevent TB outbreaks, all nonhuman primates are routinely tested for TB. At present, the standard means for detecting TB in nonhuman primates is tuberculin skin testing (TST). Unfortunately, TST has several shortcomings. Foremost, TST of nonhuman primates is extremely impractical. To test a nonhuman primate using TST, one must intradermally inject mammalian old tuberculin or tuberculin protein derivatives into the skin of an animal's upper eyelid. Because of the delicacy of this procedure, one must place an animal under deep chemical restraint or anesthesia during the injection. Following injection, one must check the eyelid at 24, 48, and 72 hours for a hypersensitivity-induced induration, the appearance of which indicates previous exposure to TB. Although one may also perform TST by intradermally injecting mammalian old tuberculin into the abdomen, abdominal injection is less desirable because it requires one to recapture the animal and palpate the test site. In contrast, induration at the eyelid causes the eyelid to swell and droop, a reaction that one may observe at a distance.

Another serious shortcoming of TST is that it lacks sensitivity. Sensitivity refers to the accuracy of a test, with which animals with a disease are correctly classified as positive. In nonhuman primates, the sensitivity of the TST is diminished by false negatives, or false negative results, reactions, or tests in which animals that do have TB fail to react as positive on the test. False negative tests are known to occur in early or advanced disease states. In advanced states, absence of delayed hypersensitivity has been attributed to anergy-absence of sensitivity to substances that would normally elicit an antigenic response. Concomitant severe illness, viral infections, such as measles, nutritional deficiencies, recent immunizations, or treatment with isoniazid—a crystalline antibacterial compound used to treat TB—may also result in false negative reactions. New world monkeys, including, but not limited to, squirrel monkeys, owl monkeys, and capuchins with TB have been reported to have a diminished hypersensitivity to tuberculin. Unfortunately, false negative tests are a major reason that TB outbreaks in nonhuman primates occur regularly in research colonies, zoos, and other facilities. These outbreaks disrupt expensive and important medical trials and lead to the destruction of many animals each year.

In addition to lacking sensitivity, TST also lacks specificity. Specificity refers to accuracy in correctly classifying a non-infected animal as negative or the absence of false positives, or false positive results, reactions, or tests in which animals that do not have TB react as positive on the test. Because of lack of specificity, TST results in numerous false positive skin tests each year. A major cause of false positive tests is believed to be cross-reactivity between some of the tuberculin antigens and nonpathogenic species of environmental mycobacteria. False positives are also known to arise from nonspecific inflammatory responses by an uninfected animal to a component of mammalian tuberculin (Butler et al., *Medical Management: Biology and Management*, (eds) Bennett, B. T., Abee, C. R., and R. Henrickson, Academis Press, San Diego, 1995; Corcoran and Jaax, *Lab Anim. Sci,* 41:57-62, 1991, Fox et al., *J. Med. Primatol.,* 11:380-388, 1982). In some instances, false positives can even occur because of microtrauma to eyelid in the course of performing the intradermal injection.

False positive and false negative reactions have been a problem with all skin tests aimed at diagnosing TB in nonhuman primates. A review of the literature from 1970 to the present reveals dozens of papers citing instances of nonhuman primates that tested positive for TB by culture of *M. tuberculosis* or *M. bovis* organisms from body tissues—the gold standard of diagnosis—while repeatedly showing no delayed hypersensitivity to mammalian old tuberculin. Other mixtures of proteins, including Koch's Old Tuberculin, BCG, and various forms of PPD (purified protein derivatives) have been tried as skin test diagnostics in nonhuman primates. All had the same propensity for false positive and false negative results (Tauraso, *Lab. Anim. Sci.* 23:201-210, 1973; Corcoran and Jaax, 1991; Chaparas et al., *Am. Ray. Resp. Dis.* 112:43-47, 1975 Baram et al., *Lab. Anim. Sci,* 21:727-733, 1971; McLaughlin et al., *Lab Anim. Sci,* 26:44-50, 1976; Stunkard et al., *Ant J. Vet. Res.* 32:1873-1878, 1971).

Because of the propensity of TST to produce false positives and negatives, current testing protocols mandate multiple testing of each nonhuman primate imported into the United States. And given that approximately 9,000 nonhuman primates are imported each year, this is a daunting task. Upon entry into the United States, each of these 9,000 animals is usually held in quarantine for at least 90 days, in part because of the frequency and persistence of false negative TST reactions (Fox et al., 1982). While in quarantine, each animal is tested every two weeks and must have a minimum of five consecutive negative TB tests before being released from quarantine. If any animal tests positive, all other animals from the same shipment must begin a new period of quarantine (Butler et al., 1995). Animals that are released from quarantine, or captive-bred nonhuman primates that are maintained in colonies in which new animals are introduced, are generally tested for TB at least quarterly. Even closed colonies in which no new animals are introduced are tested at least once or twice per year in an effort to prevent TB outbreaks.

Recognizing the shortcomings of TST and the effort and costs associated with preventing TB outbreaks, several entities involved in the management of nonhuman primate colonies, including the Center for Disease Control, the NIH, and others, have called for the development of a quick and reliable test for nonhuman primate TB. In fact, for the past several years, the United States Public Health Service has solicited grant applications on the basis that an "urgent need currently exists for the development of improved methods for the detection of active tuberculosis in nonhuman primates."

One recently developed test for nonhuman primate TB is PRIMAGAM™ (Pfizer Inc., New York, N.Y.). This test measures the cell-mediated immune response to a purified protein derivative (PPD), a crude antigen mixture that is similar to tuberculin. Specifically, two types of PPD—from *M. Bovis* and from *M. avium*—are used to trigger interferon-gamma production during TB infection. To measure interferon-gamma, PRIMAGAM™. relies on a multi-step enzyme immunoassay and spectrophotometry. Although PRIMAGAM™ is more specific than TST, it is less sensitive than TST (Garcia et al., 2004). For this reason, it has been recommended that PRIMAGAM™ be used in conjunction with TST (Garcia et al., *Comp Med.* 54(1):86-92, 2004).

Other tests have been developed to test for TB. For instance, U.S. Pat. No. 6,841,159 is directed to a lateral flow assay to detect *M. tuberculosis* and other mycobacteria. In the assay disclosed in U.S. Pat. No. 6,841,159, a nonspecific mixture of TB antigens is immobilized on a test strip. A sample of a patient's body fluid is then placed into contact with the non-specific mixture of antigens. If *M. tuberculosis* antibodies are present in the patient's sample, those antibodies form a visible antibody-antigen complex on the test strip, indicating a positive result. This test, however, is not specifically tailored to nonhuman primates. Thus, this test cannot account for animal-to-animal variations in antigen recognition patterns among nonhuman primate populations. Additionally, this test does not permit the detection of IgM antibodies in sufficient quantities to permit detection of TB antibodies early in nonhuman primate TB infection.

Accordingly, there is a need therefore for a TB test that is specifically designed for nonhuman primates. There is also a need for a nonhuman primate TB test that is less invasive than TST. Moreover, there is a need for a nonhuman primate TB test that is rapid and easy to administer. There is also a need for a nonhuman primate TB test that is more sensitive and more specific than TST. Additionally, there remains a need for a nonhuman primate TB test that needs only small amounts of test sample.

SUMMARY OF THE INVENTION

The currently available methods for detecting TB in nonhuman primates, TST, are limited, for example, in that they are impractical, nonspecific, and insensitive. Nonspecific and insensitive nature of currently available tests leads to numerous false positives and false negatives, creating a significant problem for nonhuman primate populations and humans that come into contact with those populations. The present invention alleviates these problems by providing a diagnostic method for detecting TB in nonhuman primates that is advantageous, for example, in that it is easy to use, sensitive, and specific.

In contrast to TST, which requires intradermal injection of a crude assortment of mycobacterial antigens, the present invention requires only that one remove a small amount of a test sample from a test animal. Additionally, instead of a crude antigen mixture, the present invention utilizes defined mixtures of recombinant mycobacterial antigens. By utilizing these carefully selected mixtures of antigens, the present invention overcomes animal-to-animal variations in antigen recognition patterns among nonhuman primates. Additionally, the use of specific antigenic mixtures according to the present invention enables the production of a highly sensitive nonhuman primate test for TB. To achieve even greater specificity, various embodiments of the present invention utilize defined antigen mixtures that comprise polyfusion proteins.

In a preferred embodiment, the present invention utilizes an antigen-antibody-antigen arrangement to detect TB infection in nonhuman primates. Using this arrangement, the present invention can detect IgM antibodies to TB, in addition to IgG antibodies. Because of the ability to detect IgM antibodies, the present invention provides the ability to detect TB earlier in nonhuman primate TB infection as compared to conventional TB tests. Because of the highly contagious nature of TB, early detection of TB is critical to the effective management of nonhuman primates.

The present invention further combines specific antigen mixtures with a lateral flow platform. A lateral flow platform enables production of a test that is rapid and easy to use. Additionally, a lateral flow format permits the combination of different antigen mixtures that provide an even greater level of sensitivity, particularly as compared to conventional methods. Increased sensitivity of the present invention enables the production of a single test that has a low occurrence of false negatives as compared to conventional methods.

Accordingly, it is an object of the present invention to provide a practical and easy-to-use method for detecting the presence of antibodies to mycobacterial antigens in nonhuman primates.

Another object of the present invention is to provide a practical and easy-to-use method for diagnosing TB in nonhuman primates.

It is another object of the present invention to provide a reliable nonhuman primate TB diagnostic method that is highly specific and sensitive.

Yet another object of the present invention is to identify mycobacterial antigens that are most frequently recognized in nonhuman primate TB infections.

It is another aspect of the present invention to provide recombinant polyfusion mycobacterial-based antigens that are most frequently recognized in nonhuman primate TB infections.

Another object of the present invention is to provide a TB test that is sensitive to IgM antibodies and other immunoglobulins and that can therefore detect early TB infection in nonhuman primates.

It is yet another aspect of the present invention to provide recombinant polyfusion mycobacterial-based antigens that are most frequently recognized in nonhuman primate TB infections, wherein such antigens comprise polyfusion proteins, including, but not limited to, TBF10, CFP10/ESAT6, and Arc1/MPB83 (or Arc1/MPT83).

Another object of the present invention is to design a mixture of selected mycobacterial antigens that are both specific and sensitive to TB infection in nonhuman primates.

Still another object of the present invention is to provide a rapid lateral flow assay for detecting TB in nonhuman primates.

Another object of the present invention is to provide a rapid lateral flow assay for detecting TB in nonhuman primates that requires only a small volume of test sample.

Yet another object of the present invention is to provide a lateral flow assay for detecting TB in nonhuman primates that is safe.

These and other objects, features and advantages of the present invention will become apparent after a review of the following detailed description of the disclosed embodiment and the appended claims.

DETAILED DESCRIPTION OF THE INVENTION

The present invention may be understood more readily by reference to the following detailed description of specific embodiments included herein. Although the present invention has been described with reference to specific details of certain embodiments thereof, it is not intended that such details should be regarded as limitations upon the scope of the invention. The entire text of the references mentioned herein is hereby incorporated in their entirety by reference, including U.S. Provisional Application Ser. No. 60/605,304 filed Aug. 26, 2004.

As Table 2 below illustrates, immune recognition of TB antigens varies considerably from animal-to-animal in nonhuman primates. In fact, there is currently no known single antigen that is recognized by all nonhuman primates. To overcome this animal-to-animal variation among nonhuman primates, the present invention employs novel and defined mixtures of TB antigens. In particular, the individual antigens of the antigen mixtures work collectively to provide unique epitope panels that are immunoreactive across nonhuman primate populations.

In selecting antigens according to the present invention, preferable antigens possess individual seroreactivity, i.e., each antigen of a mixture is recognized by at least one-fourth of TB-infected nonhuman primates in a controlled test. Additionally, antigens according to the present invention may react with test samples that are negative when reacted with other selected antigens. Antigens according to the present invention are also specific, i.e., they do not cross-react with test samples from uninfected nonhuman primates (thus resulting in a false positive). Preferable antigens according to the present invention also elicit higher antibody responses as compared to at least some of the other antigens, and/or do not compete/interfere with at least some of other antibodies in the mixture, and/or are typically reactive early in the course of a TB infection. By utilizing specific mycobacterial antigen mixtures with some or all of these characteristics, the antigen mixtures according to the present invention are reactive with a wide spectrum of nonhuman primate antibodies and are hence recognized by sera from a vast majority of TB-infected nonhuman primates.

While not wishing to be bound to any particular method of selecting antigens according to the present invention, a preferable method for selecting such antigens is the Multi-Antigen Print ImmunoAssay (MAFIA) as described in Lyashchenko et al., *J. Immunol. Methods* 242:91-100, 2000. This method is based on immobilization of multiple antigens to nitrocellulose membranes, followed by antibody detection using standard chromogenic immunodevelopment known in the art. Unlike other immunoassays, such as ELISA, the MAFIA also offers fast screening of multiple antigens. The MAFIA allows simultaneous testing of multi-antigen mixtures and single antigens on the same strip using the same serum sample. As Tables 2-4 below illustrate, the MAFIA screening allows the identification of several antigens that are recognized by nonhuman primate serum IgG. Additionally, the MAPIA screening permits the identification and subsequent selection of the TB antigens that are most reactive among nonhuman primate populations.

Although the present invention may employ a variety of different mycobacterial antigens known in the art (Lyashchenko et al., *Infect Immun.* 72(5):2462-7, 2004; Whelan et al., *Infect Immun.* 71(11):6420-5, 2003), antigenic protein mixtures according to certain embodiments of the present invention may comprise one or more of ESAT-6, CFP1O, Mo-29, Mtb8, Arc1, 38 KDa, Mtb48, MPB70, MPT70, MPB83, MPT83, MPT63, MPB63, MPB64 and MPT64 or any combinations thereof. More preferably, certain embodiments of the present invention may comprise ESAT-6, CFP10, and MPB83. Additionally, antigenic proteins according to certain embodiments of the present invention may comprise various polyprotein fusions of one or more of ESAT-6, CFP10, Mo-29, Mtb8, Arc1, 38 KDa, Mtb48, MPB70, MPT70, MPB83, MPT83, MPT63, MPB63, MPB64 and MPT64 or any combinations thereof. In a preferred embodiment of the present invention, the antigenic proteins comprise MPB83 (or MPT83), TBF10, CFP10/ESAT-6, and Arc1/MPB83 (or Arc1/MPT83). TBF10 is a three-protein construct and includes sequences of Mtb8, CFP10, and the 38 kDa protein of *Mycobacterium tuberculosis*. Hybrids CFP10/ESAT-6 and Acr1/MPB83 are two-protein molecules representing the corresponding sequences. One may use any method known in the art to make the polyfusion proteins of the present invention. And because all of the antigenic epitopes described herein are present in *M. tuberculosis* and *M. bovis*, they are reactive with antibodies produced in TB caused by either microorganism.

In various embodiments of the present invention, specific mycobacterial antigen mixtures are immobilized onto a membrane at one or more locations to form one or more test lines or test areas. One skilled in the art will appreciate that a number of different membranes are suitable for immobilizing antigens, including, for example, nylon, polyvinyl difluoride, or nitrocellulose membranes. Preferably, the membrane is a nitrocellulose membrane having pore sizes of about 1 μm to about 25 μm or a flow rate of about 30 sec to about 400 sec per 1-10 cm. Preferably, the membrane is a nitrocellulose membrane having pore sizes of about 3 μm to about 15 μm or a flow rate of about 80 sec to about 200 sec per 4 cm. Immobilization of the antigen mixtures is possible by any method known in the art. For example, one may immobilize antigens onto the membrane with a semiautomated airbrush printing device (Linomat IV; Camag Scientific, Inc., Wilmington, Del.).

In a separate step, one obtains a test sample from the animal to be tested. The test sample can be any sample capable of containing antibodies to mycobacterial antigens. Preferably, the test sample comprises whole blood or serum. Alternatively, the test sample may comprise any other bodily fluid, including, but not limited to urine, saliva, or sputum. The test sample is then incubated with particles coated with a compound capable of indiscriminately binding the protein-coated particles to IgG antibodies within the test sample, such as, but not limited to, Protein A, Protein G, Protein A/G, or, for example, nonhuman primate anti-IgG. The particles may comprise colloidal gold or colored latex. The incubation step facilitates the indiscriminate binding of the protein coated particles to IgG antibodies within the test sample, thus forming IgG-Particle complexes. To facilitate mixing of the test sample with the protein coated particles, the test sample may optionally be diluted using a sample buffer. Sample buffers compatible with the present invention include, but are not limited to, any buffers known in the art that do not cause antibody-antigen dissociation. For example, a compatible sample buffer may comprise phosphate buffered saline (PBS), Tris-Buffered Saline (TBS), or HEPES buffer at a pH from about 7.5 to about 9.5, or more preferably around pH of 8.0. Additionally, sample buffers compatible with the present invention may comprise low amounts of a detergent such as Tween 20 (about 0.1%).

Following the formation of IgG-Particle complexes, one may optionally wash the IgG-Particle complexes with sample buffer to remove contaminants that may affect specificity of the assay. After the optional wash step, the IgG-Particle complexes are applied over the membrane. If the IgG-Particle complexes contain antibodies specific for the antigen mixtures immobilized on the membrane, the IgG-Particle complexes will bind to the membrane at the one or more test lines or test areas. To prevent nonspecific binding of the of the IgG-Particle complexes to the membrane, the membrane may be blocked before the application of the IgG-Particle complexes with a solution of one or more blocking agent, for example, but not limited to, a solution of milk, bovine serum albumin (BSA), or other blocking agents know in the art. In an embodiment of the present invention, binding of the IgG-Particle complexes to the test lines or areas results in a visible signal as follows. The immobilized antigens are not themselves visible, nor are the IgG-Particle complexes. But because the IgG-Particle complexes comprise colloidal gold or colored latex, the aggregation of a large number of particles on the membrane becomes visible to the human eye. Other suitable methods of visualization may also be employed in embodiments of the present invention. Visualization of the aggregated particles confirms the presence of mycobacterial antibodies in the test sample, indicating a positive test for TB infection.

In a preferred embodiment, the invention comprises an antigen-antibody-antigen arrangement to provide increased sensitivity. In this embodiment, at least one first specific mixture of mycobacterial antigens is immobilized on a membrane to form a test line or test area. Additionally, a second specific mycobacterial antigen mixture is conjugated to colored particles, such as, but not limited to, latex particles, to form antigen-particle conjugates. In this embodiment, antibodies in the test sample are brought in contact with, in solution or otherwise, and bind specifically (rather than indiscriminately) to the antigens conjugated to the particles to form antibody-antigen-particle complexes. After formation of antibody-antigen-particle complexes, one may optionally wash the antibody-antigen-particle complexes with a sample buffer as described above. After the optional washing step, the antibody-antigen-particle complexes are applied to the membrane. Antibodies of the antibody-antigen-particle complexes that are specific for antigens in the first specific mixture of mycobacterial antigens will bind to the membrane at the test line or test area. Not wishing to be bound by any particular theory of a binding, it is believed that the antibodies of the antibody-antigen-particle complex form a bridge structure to the first mycobacterial antigens immobilized on the membrane. To prevent nonspecific binding of the antibody-antigen-particle complexes to the membrane, the membrane may be blocked before the application of the antibody-antigen-particle using one or more blocking agent, for example, but not limited to, a solution of milk, bovine serum albumin (BSA), or other blocking agents know in the art. Aggregation of the antibody-antigen-particle complexes at a test line or test area results in a visible signal.

In the antigen-antibody-antigen embodiments of the present invention, one may manipulate the composition of the first and second mixtures of antigens to optimize sensitivity. As shown in Table 1 below, which relies on latex as the particle, the first antigen mixture may comprise MPB83 (or MPT83), TBF10, and CFP10/ESAT6, while the second antigen mixture may comprise BF10, CFP10/ESAT6, and Arc1/MPB83 (or Arc1/MPT83).

TABLE 1

Compositions of Antigens

| Protein | Type | Location |
| --- | --- | --- |
| MPB83 | Single | Latex |
| TBF10 | Fusion | Latex and membrane |
| CFP10/ESAT6 | Fusion | Latex and membrane |
| Acr1/MPB83 | Fusion | Membrane |

One significant advantage of the antigen-antibody-antigen arrangements is that they permit the detection of IgM in addition to IgG and other immunoglobulins. This is important because the first humoral immune response to TB infection involves IgM, followed by IgG. Thus, by detecting IgM, the present invention can diagnose TB during early infection stages.

Certain aspects and embodiments of the present invention provide systems, composition, and methods for detection of mycobacterial infections, such as tuberculosis, in non-human primates. Certain embodiments of the present invention may use one or more support, such as but not limited to membranes, that allow capillary flow of liquids along the support. Apparatuses and methods that use a solid support allowing capillary flow of liquids along the support may also be referred to as lateral flow platforms, systems, tests, assays, or devices. According to certain embodiments of the present invention, various immunoreactive molecules, such as, but not limited to, antigens, including one or more of mycobacterial antigens, antibodies, such as IgG, or molecules capable of unspecifically binding antibodies, such as Protein A, Protein G, Protein AG, or Protein L may be immobilized on a solid support allowing capillary flow of liquids.

In certain embodiments of the present invention, the specific antigen mixtures may be used in combination with a lateral flow platform to provide a rapid and easy format for detecting TB in nonhuman primates. This format also increases the safety of handling test sample because the test sample is contained within the lateral flow device for the majority of the assay. Several lateral flow platforms are known in the art (for example, see Fong et al., *J. Clin. Microbiol.*, 38(7):2525-9, 2000; U.S. Pat. No. 4,956,302), and each generally comprise a pad, a membrane, and a housing or casing. The housing usually contains window for viewing the assay results. In certain embodiments of the present invention, the housing of the lateral flow platform may have a barrel shape.

In one lateral flow embodiment of the present invention, an antigen mixture is immobilized onto a membranous strip at one or more locations to form at least one test line or test area. One may immobilize antigens onto the membrane by any method known in the art, such as by the semiautomated airbrush printing device (Linomat IV; Camag Scientific, Inc., Wilmington, Del.) as noted above. Following immobilization of antigens onto the membrane, a test sample is applied to a pad at the end of the membranous strip. If the sample is whole blood, it may first pass through a blood filter that retains the cellular elements, allowing the serous portion of the sample to pass through to the membrane. To facilitate migration of the test sample through the pad and along the membrane strip, one may optionally dilute the sample with a sample buffer as described herein.

As the test sample passes through the pad, it comes into contact with particles that are located on or within the pad. The particles can be colloidal gold or latex and are coated with Protein. A, Protein G, Protein A/G, or, for example, nonhuman primate anti-IgG, to capture all of the IgG antibodies, regardless of their specificity. The particles, now bristling with nonhuman primate antibodies, are propelled through the membrane by capillary forces, and ultimately flow towards a test line or test area. If the particles contain antibodies to the antigens immobilized on the membrane, they will be trapped at the test line or test area. Conversely, particles that lack antibodies to the mixture of antigens continue to flow until they reach the control line, which is imprinted, in one embodiment, with Protein A, Protein G, or Protein A/G or other trapping agent. The particles that reach the control line are trapped at the control line location because of the affinity of the IgG for Protein A, Protein G, or Protein A/G. The immobilized antigens and the control line are not themselves visible, nor are the particles when they are flowing along the membrane. In one variant of the present invention, when a large number of particles aggregate at a single point (i.e., a test line or control line) do they become visible to a human eye.

In another lateral flow embodiment of the present invention, the antigen-antibody-antigen arrangement is employed to achieve increased sensitivity and specificity. In this embodiment, at least one first mixture of mycobacterial antigens is immobilized at one or more locations on a membranous strip of a lateral platform. Additionally, a second specific mycobacterial antigen mixture is conjugated to colored particles, such as latex particles, to form antigen-particle conjugates. In this embodiment, addition of a test sample containing specific antibodies to the antigen-particle conjugates results in the formation of an antibody-antigen-particle complex. The antibody-antigen-particle continues to migrate toward the test line or test area. If antibodies have been specifically captured by the antigen-particle conjugate, the resultant antibody-antigen-particle complex will bind to the first mixture of antigens immobilized on the membrane. Aggregation of multiple antibody-antigen-particle complexes will result in a visible signal. In the absence of antibodies, there is no visible signal at the test line or test area. After passing the test line or test area, the antigen-particle conjugates, and perhaps some antibody-antigen-particle complexes, may continue to migrate to a control line or area. As a control, antibodies specifically directed to the antigens conjugated to the particles may be printed on the membrane downstream for the test line or area to form a control line; as the antigen coated particles pass the control line, the antigen coated particles will bind to the antibodies of the control line, trapping the particles at the control line. Alternatively, the control line may comprise Protein A, Protein G, or Protein A/G. Preferably, IgG may be conjugated to the particles while the downstream control line comprises anti-IgG. In this embodiment, the conjugated IgG may be purified rabbit IgG while the printed control line comprises goat-anti-rabbit IgG. The assay is read visually within about 20 minutes and a positive result can be recorded semi-quantitatively. Any visible test line or test area in the presence of a visible control line is considered a positive result. To facilitate migration of test sample through the pad and along the membrane, the one may optionally dilute the test sample with a sample buffer as described herein. Additionally, to reduce nonspecific binding to the membrane, the sample buffer diluent may contain a blocking agent such as milk or BSA, or more preferably, 5-8% fish serum.

As noted above, the present invention may employ a variety of different mycobacterial antigens. But while a variety of antigens are compatible with the present invention, it has been found that antigen mixtures comprising polyfusion proteins are particularly advantageous. Specifically, antigenic protein mixtures comprising polyfusion proteins tend to perform better than corresponding nonfusion proteins, especially in membrane-based antibody detection assays as described herein. The test lines or test areas obtained with positive samples are often stronger and sharper, resulting in a greater signal-to-noise ratio. With less noise, the assays are easier to read. While not wishing to be bound by any particular theory accounting for this phenomenon, it is believed that the stronger and sharper positive signals obtained with polyfusion proteins results from the combined effect of (1) a more robust retention on the membrane of molecules with higher molecular mass and (2) a decreased level of sequestration or denaturation of critical epitopes during antigen coating onto the membrane, resulting in a better epitope exposure. Similarly, in the antigen-antibody-antigen embodiments of the present invention, the use of polyfusion proteins may also decrease the level of sequestration or denaturation of critical epitopes during coating of the polyfusion proteins onto the particles. In some instances, low-level antibody responses that could not be detected with nonfusion proteins were detected by a detection method using a polyfusion protein, demonstrating that polyfusion proteins or combination thereof confer greater sensitivity to detection methods. Increased sensitivity is particularly important in nonhuman primates, where the proportion of TB infected animals that produce weak antibody responses may be relatively large. Additionally, the use of polyfusion proteins results in time and cost savings because one does not have to expend time and resources to manufacture multiple, single proteins.

Diseases and Conditions to be Treated

The methods and compositions described herein may be adapted useful for detecting TB infections in nonhuman primates. As used herein, the term "non-human primate" denotes all non-human living primates according to any or all of various classifications of non-human living primates, including, but not limited to, families Callitrichidae (marmosets and tamarins), Cebidae (New World monkeys), Cercopithecidae (Old World monkeys), Cheirogaleidae (dwarf lemurs and mouse lemurs), Daubentoniidae (aye-aye), Galagonidae (bushbabies and galagos), Hominidae (including great apes), Hylobatidae (gibbons and lesser apes), Indridae (indris, sifakas, and relatives), Lemuridae (true lemurs), Loridae (lorises), Megaladapidae (sportive lemurs), and Tarsiidae (tarsiers). The term "non-human primates" encompasses non-human primates and groups thereof classified according to any or all of various classifications of non-human living primates. For example, Wilson and Reeder (1993) split Megaladapidae from Lemuridae, Galagonidae from Loridae (and in spelling the latter Loridae rather than Lorisidae), and include the great apes in Hominidae. Wilson, D. E., and D. M. Reeder. 1993. Mammal Species of the World, A Taxonomic and Geographic Reference. 2nd edition. Smithsonian Institution Press, Washington. Anderson and Jones (1984) divide the order of living primates (Primates) into two suborders, the Strepsirhini and the Haplorhini. Thorington, R. W., Jr., and S. Anderson. 1984. Primates. Pp. 187-217 in Anderson, S. and J. K. Jones, Jr. (eds). Orders and Families of Recent Mammals of the World. John Wiley and Sons, N.Y. The Strepsirhines include mostly arboreal species with many primitive characteristics, but at the same time, some extreme specializations for particular modes of life, and wherein the Haplorhines are the so-called "higher" primates, further divided into two major groups, the Platyrrhini and the Catarrhini. Platyrrhines have flat noses, outwardly directed nasal openings, three premolars in upper and lower jaws, anterior upper molars with 3 or 4 major cusps, and are found only in the New World (families Cebidae and Callitrichidae). Catarrhines have paired downwardly directed nasal openings, which are close together; usually two premolars in each jaw, anterior upper molars with 4 cusps, and are found only in the Old World (Cercopithecidae, Hylobatidae, Hominidae). Most primate species live in the tropics or subtropics, although a few also inhabit temperate regions. Except for a few terrestrial species, primates are arboreal. Some species eat leaves or fruit; others are insectivorous or carnivorous. See Myers, P. 1999. "Primates" (On-line), Animal Diversity Web. Accessed Aug. 26, 2005. It is to be understood that the foregoing classification is non-limiting and includes past, present, and future variations and changes as known to those skilled in the art.

Furthermore, the methods and compositions described herein are useful for detecting TB caused by mycobacteria, such as, *Mycobacterium tuberculosis, Mycobacterium bovis, Mycobacterium avium-intracellulare, Mycobacterium kansaii, Mycobacterium fortuitum, Mycobacterium chelonae, Mycobacterium leprae, Mycobacterium africanum*, and *Mycobacterium microti*. The methods and antigen mixtures described herein, however, are particularly suited for detecting TB and TB-like infections caused by *Mycobacterium tuberculosis, Mycobacterium bovis*, and *Mycobacterium africanum*, with limited cross-reactivity to *Mycobacterium kansasii*. The following examples illustrate various embodiments and aspects of the present invention, but are not to be construed as limiting the scope of the present invention in any way.

DEFINITIONS

The terms "a", "an" and "the" as used herein are defined to mean one or more and include the plural unless the context is inappropriate.

As used herein, the phrase "mycobacterial antigen" is defined to encompass all antigenic epitopes, proteins, protein fragments and peptides associated with all mycobacteria including, but not limited to, *Mycobacterium tuberculosis, Mycobacterium bovis, Mycobacterium avium-intracellulare, Mycobacterium kansaii, Mycobacterium fortuitum, Mycobacterium chelonae, Mycobacterium leprae, Mycobacterium africanum*, and *Mycobacterium microti*.

The term "antigen" or "antigenic" is defined herein as an entity capable of eliciting an immune reaction in vivo or in vitro assays or other known techniques.

The term "peptides" describes chains of amino acids (typically L-amino acids) whose alpha carbons are linked through peptide bonds formed by a condensation reaction between the carboxyl group of the alpha carbon of one amino acid and the amino group of the alpha carbon of another amino acid. In naturally occurring peptides, in most cases, the terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free alpha-amino group on the amino acid at the amino terminal of the peptide, or to the alpha-amino group (amido group when participating in a peptide bond) of an amino acid at any other location within the peptide. Similarly, the term "carboxy terminus" (abbreviated C-terminus) refers to the free carboxyl group on the amino acid at the carboxy terminus of a peptide, or to the carboxyl group of an amino acid at any other location within the peptide.

Typically, the amino acids making up a peptide are numbered in order, starting at the amino terminal and increasing in the direction toward the carboxy terminal of the peptide. Thus, when one amino acid is said to "follow" another, that amino acid is positioned closer to the carboxy terminal of the peptide than the preceding amino acid. Here, naturally occurring amino acids are represented in the text by the commonly used one letter codes (e.g. G=glycine).

The term "residue" is used herein to refer to an amino acid (D or L enantiomer) that is incorporated into a peptide by an amide bond. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

Furthermore, one skilled in the art will recognize that, as mentioned above, individual substitutions, deletions or additions which alter, add or delete a single amino acid or several amino acids in a sequence are conservatively modified variations where the alterations result in the substitution of an amino acid with a chemically similar amino acid. Conservative substitution tables providing functionally similar amino acids are well known in the art. The following six groups each contain examples of amino acids that are frequently considered as conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K); Glutamine (Q);
5) Isoleucine (I), Leucine (L), Methionine (M), Valine (V);
6) Phenylalanine (F), Tyrosine (Y), Tryptophan (W).

Typically, the isolated, antiproliferative peptides described herein are at least about 80% pure, usually at least about 90%, and preferably at least about 95% as measured by HPLC.

When peptides are relatively short in length (i.e., less than about 50 amino acids), they are often synthesized using chemical peptide synthesis techniques. Solid phase synthesis is a method in which the C terminal amino acid of the sequence is attached to an insoluble support followed by sequential addition of the remaining amino acids in the sequence. This is a preferred method for the chemical synthesis of the peptides described herein. Techniques for solid phase synthesis are known to those skilled in the art.

Short peptides and related amides can also by synthesized efficiently by solution phase coupling chemistry. Amino acids and related molecules, with the appropriate protection groups, are coupled in solution to yield amides and peptides. Coupling reagents for forming amide bonds include, but are not limited to, 1,3-dicyclohexyl carbodiimide, 1-hydroxybenzotriazole and N,N-diisopropylethyl amine or carbonyl diimidizole.

The term "bodily fluid," as used herein, includes, but is not limited to, saliva, gingival secretions, cerebrospinal fluid, gastrointestinal fluid, mucous, urogenital secretions, synovial fluid, blood, serum, plasma, urine, cystic fluid, lymph fluid, ascites, pleural effusion, interstitial fluid, intracellular fluid, ocular fluids, seminal fluid, mammary secretions, and vitreal fluid, and nasal secretions.

The mycobacterial antigens of the present invention may be synthesized by chemical or biological methods, such as cell culture, recombinant gene expression, and peptide synthesis. Recombinant techniques include gene amplification from DNA sources using the polymerase chain reaction (PCR), and gene amplification from RNA sources using reverse transcriptase/PCR. Peptides and proteins of interest can be extracted from body fluids by known protein extraction methods, particularly the method described by Novotny, W. F., et al., J. Biol. Chem. 264:18832-18837 (1989).

Peptides or Protein Fragments

Peptides or protein fragments comprising mycobacterial antigens can be produced as described above and tested for antigenic activity using techniques and methods known to those skilled in the art. Full length proteins can be cleaved into individual domains or digested using various methods such as, for example, the method described by Enjyoji et al. (Biochemistry 34:5725-5735 (1995)) which is incorporated herein by reference in its entirety.

Alternatively, fragments are prepared by digesting the entire protein, or large fragments thereof exhibiting antigenic activity, to remove one amino acid at a time. Each progressively shorter fragment is then tested for antigenic activity. Similarly, fragments of various lengths may be synthesized and tested for antigenic activity. By increasing or decreasing the length of a fragment, one skilled in the art may determine the exact number, identity, and sequence of amino acids within the protein that are required for antigenic activity using routine digestion, synthesis, and screening procedures known to those skilled in the art.

Also included in the present invention are peptides having conservatively modified variations in comparison to the claimed peptides, wherein the activity of the peptide is not significantly different from that of the claimed peptide.

The compositions and methods are further illustrated by the following non-limiting examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims. The following experiments were conducted using methods and protocols well known to those skilled in the art. Details regarding the procedures used are found throughout the scientific literature and also for example in United States patents.

EXAMPLE 1

Selection of Antigens

Figure 1:
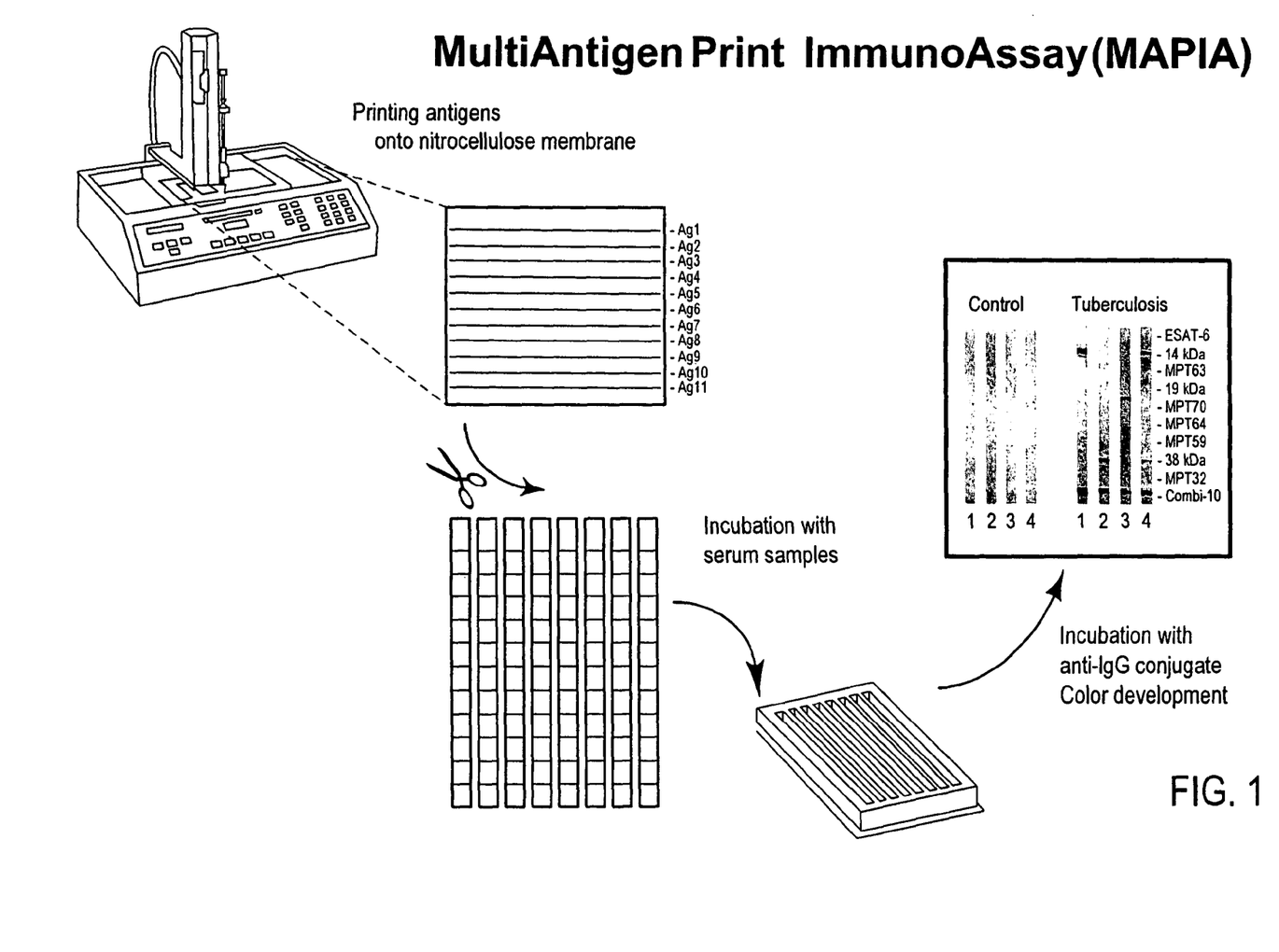
FIG. 1 is a schematic of MAPIA assay, including a photograph of a Western blot-like chromogenic immunodevelopment of results of testing of recombinant antigens of *M. tuberculosis* and polyepitope fusion proteins.

Mycobacterial antigens of the present invention were selected using Multi-Antigen Print ImmunoAssay (MAPIA) as described in Lyashchenko et al., 2000. Briefly, antigens were immobilized on a nitrocellulose membrane (Schleicher & Schuell BioScience, Inc. USA, Keene, N.H.) at a protein concentration of 0.05 mg/ml by using a semiautomated airbrush printing device (Linomat IV; Camag Scientific, Inc., Wilmington, Del.). The membrane was cut perpendicular to the antigen bands into 4-mm-wide strips. The strips were blocked for 1 h with 1% nonfat skim milk in PBS, pH 7.2, with 0.05% Tween 20 and then incubated for 1 h with serum samples diluted 1:50 in blocking solution. After being washed, the strips were incubated for 1 h with alkaline phosphatase-conjugated anti-human immunoglobulin G antibody (Sigma Chemical Co., St. Louis, Mo.) diluted 1:5,000 in blocking solution, followed by another washing step. Bound antibodies were visualized with 5-bromo-4-chloro-3-indolylphosphate-nitroblue tetrazolium (BCIP-NBT) (Kirkegaard & Perry Laboratories, Gaithersburg, Md.). FIG. 1 shows results of identification of several TB antigens in the MAPIA assay.

EXAMPLE 2

Serological Responses in Monkey Tuberculosis

Figure 2:
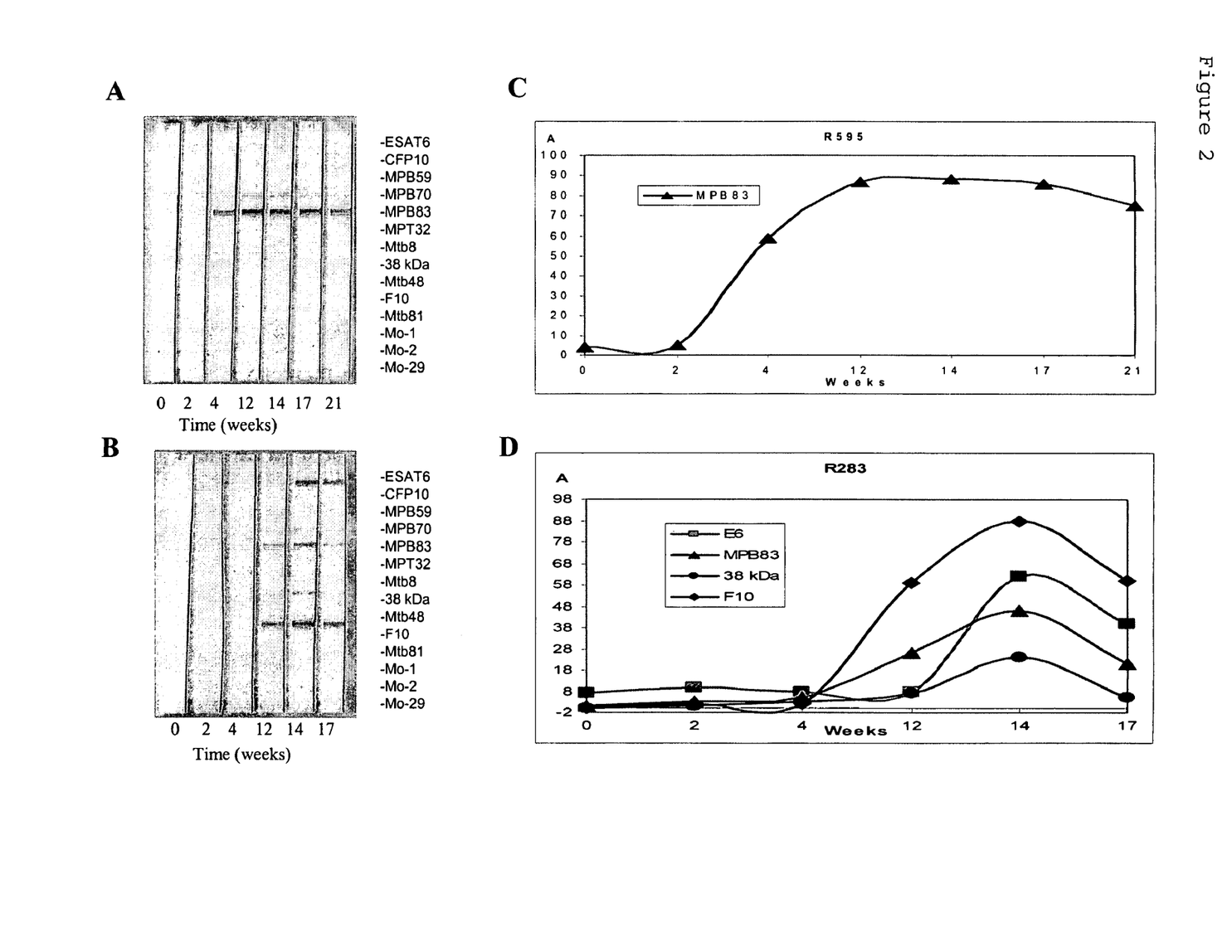
FIG. 2 shows in Panels A and B photographs of results of antibody responses in rhesus monkeys experimentally infected with *M. tuberculosis* and in Panels C and D, plots of antibody responses in rhesus monkeys experimentally infected with *M. tuberculosis* are shown.

In MAPIA, 14 infected monkeys produced IgG antibodies of variable levels and starting at various time-points post-infection. FIG. 2. As shown in Table 2-4 below, antigen recognition patterns varied significantly from animal to animal. Three proteins, ESAT-6, MPB83, and TBF10 were most often recognized by post-infection serum samples.

TABLE 2

Antigen recognition patterns in *M. tuberculosis* infection

| Antigen | Animal # | | | | | | | | | | | | | |
|---|---|---|---|---|---|---|---|---|---|---|---|---|---|---|
| | 056 | 209 | 283 | 304 | 590 | 595 | 653 | 727 | 729 | 814 | 847 | 855 | 861 | 867 |
| ESAT6 | | | | | | | ▒ | ▒ | ▒ | ▒ | | ▒ | | ▒ |
| CFP10 | | ▒ | ▒ | | | ▒ | | ▒ | | | | ▒ | | |
| Mo-1 | | | | | | | | | | | | | | |
| Mo-2 | | | | | | | | | | | | | | |
| Mo-29 | | | ▒ | | | | | ▒ | | ▒ | | | | |
| Mtb8 | | | | ▒ | | | | ▒ | | | | | | |
| 38 kDa | | ▒ | | | | | | | | | | | | |
| Mtb48 | | | | | | | | | | | | | | |
| MPB70 | ▒ | | ▒ | | | | | ▒ | | | | | | |
| MPB83 | ▒ | | | | | | ▒ | ▒ | | ▒ | ▒ | | ▒ | |
| MPB59 | | | | | | | | | | | | | | |
| MPT32 | | | | | | | | | | | | | | |
| Mtb81 | | | | | | | | | | | | | | |
| TBF10 | | ▒ | ▒ | | ▒ | | | ▒ | | ▒ | ▒ | | | |
| TBF6 | | ▒ | | | ▒ | | | | | ▒ | | | | |
| Any antigen | ■ | ■ | ■ | ■ | ■ | ■ | ■ | ■ | ■ | ■ | ■ | ■ | ■ | ■ |

Antigen recognition is indicated by ▒ cells.

TABLE 3

Antigens predominantly recognized in experimental TB*

| M. tuberculosis | Animal ID# | ESAT6 | MPB83 | TBF10 |
|---|---|---|---|---|
| Erdman 30 CFU | 209 |  | - |  |
|  | 283 | ++ | + | +++ |
|  | 304 | + |  |  |
|  | 653 | - | - |  |
| Erdman 100 CFU | 814 | + |  | ++ |
|  | 847 | + |  | + |
|  | 855 |  |  | +++ |
|  | 861 | - | - | - |
|  | 867 |  | + | - |
| H37Rv 210 CFU | 056 | - |  | - |
|  | 590 |  | - | - |
|  | 595 | - |  | - |
|  | 727 | + |  |  |
|  | 729 |  |  |  |
| Total number of reactors |  | 10 | 11 | 9 |
| Number of earliest antibody reactors |  | 5 | 10 | 7 |

*Antigens eliciting earliest antibody are shown in ▓. Results are shown as negative (−) or Positive (+, weak; ++ moderate; +++, strong).

TABLE 4

Antigen recognition by serum IgG in monkey TB

| Antigen | Antibody reactors Number | % |
|---|---|---|
| ESAT-6 | 10 | 71 |
| CFP10 | 7 | 50 |
| Mo-1 | 0 | 0 |
| Mo-2 | 0 | 0 |
| Mo-29 | 3 | 21 |
| Mtb8 | 2 | 14 |
| 16 kDa | 6 | 43 |
| 38 kDa | 1 | 7 |
| Mtb48 | 1 | 7 |
| MPB70 | 5 | 36 |
| MPB83 | 11 | 79 |
| MPB59 | 0 | 0 |
| MPT32 | 0 | 0 |
| Mtb81 | 0 | 0 |
| F10 | 9 | 64 |
| CFP10/ESAT-6 | 10 | 71 |
| 16 kDa/MPB83 | 12 | 86 |

EXAMPLE 3

Specific Antigen Mixtures in Protein a Lateral Flow Assay

An antigen mixture consisting of the three selected proteins was formulated and evaluated in the lateral flow format. Printing conditions were optimized for ESAT-6, MPB83, and TBF10 separately by spraying each antigen at various concentrations onto the membrane, both singly and in mixtures, and selecting one concentration for each antigen that resulted in the strongest discrimination between selected TB positive and negative serum samples. A mixture of the antigens was then printed onto nitrocellulose membrane at concentration of 1 mg/ml. Protein A was printed onto the membrane as an additional line to produce the control line. Protein A was also conjugated to colloidal gold particles following routine procedures known in the art and was used as the nonhuman primate IgG antibody-detecting molecule in the lateral flow immunoassay. Test strips were laminated, such that a conjugate pad was placed between the sample pad and the nitrocellulose membrane. Strips then were placed into a standard plastic cassettes used in the art. To detect antibody in serial serum specimens collected during experimental infection of Rhesus macaques, 5 µl of each monkey serum (i.e., the test sample) was transferred onto the sample pad, followed by adding 4 drops (approximately 160 µl) of sample buffer diluent. If a test line of any intensity developed in the test window within 15 minutes, the result was considered positive. No test lines were found in pre-infection sera from any of the animals. Test bands obtained with sera of the five infected monkeys appeared within 2 to 5 minutes.

EXAMPLE 4

Conjugation of Antigen Mixtures to Latex Beads

Latex was purchased as a 10% solid suspension of beads. It was comprised of carboxylate modified polystyrene with a bead diameter of 300 nm. To 1000 µl of this suspension, 8 ml of wash buffer (2-(N-morpholino)-ethanesulfonic acid, (MES), pH=5.5+0.1) was added. The latex was sonicated, centrifuged, decanted and resuspended twice. Following washing, the latex was activated by incubating it for one hour with a freshly prepared cross-linking solution (10% 1-Ethyl-30-(3-dimethylaminopropyl)carbodiimide hydrochloride (EDC) in Type II water). The activated latex was then added to the antigen solution, resulting in a 60% (w/v) solution of antigen. The antigen solution was composed of three antigens, MPB83, CFP10/ESAT-6 and TBF10. The mixture was incubated for 1.0 hr with agitation, resulting in a conjugated latex. The conjugated latex was then blocked by adding Conjugate Wash buffer (Tris, Tween20, bovine serum albumin (BSA) solution at pH=8.0±0.1) and incubating for an additional 15 min. The blocked, conjugated latex was then washed three times and finally resuspended in 4 ml of Conjugate Wash buffer. Final conjugated latex was standardized by measuring the optical density at 590-680 nm. The material was stored until use at 2-8° C.

EXAMPLE 5

Specific Antigen Mixtures in Latex-Antigen-Antigen Lateral Flow Assay

An antigen mixture consisting of the three selected proteins was formulated and evaluated in the lateral flow format. Printing conditions were optimized for CFP10/ESAT-6, MPB83, and TBF10 separately by spraying each antigen at various concentrations onto the membrane, both singly and in mixtures, and selecting one concentration for each antigen that resulted in the strongest discrimination between selected TB positive and negative serum samples. A mixture of the antigens was then printed onto nitrocellulose membrane at concentration of 1 mg/ml. Goat Anti-rabbit was printed onto the membrane as an additional line to produce the control line. Three antigens MPB83, CFP10/ESAT-6 and TBF10 were also conjugated to latex particles according the conjugation method described in this invention. Test strips were laminated, such that a conjugate pad was placed between the sample pad and the nitrocellulose membrane. Strips then were placed into a standard plastic cassettes used in the art. To detect antibody in serial serum specimens collected during experimental infection of Rhesus macaques, 30 μl of each monkey serum (i.e., the test sample) was transferred onto the sample pad, followed by adding 3 drops (approximately 110 μl) of sample buffer diluent. If a test line of any intensity developed in the test window within 20 minutes, the result was considered positive. No test lines were found in pre-infection sera from any of the animals. It is worth noting that test bands obtained with sera of the five infected monkeys appeared within 2 to 5 minutes.

As shown in Table 5, in the antigen-antibody-antigen latex lateral flow format, serological performance of polyfusion CFP10/ESAT-6 was better than single antigens. As shown in Tables 6 and 7, the antigen-antibody-antigen latex lateral flow format was found to be highly specific and sensitive among different nonhuman primate colonies and across nonhuman primate species. As shown in Table 8, when compared to TST and PRIMAGAM™ in *M. bovis* outbreak, the antigen-antibody-antigen latex lateral flow format was found to be more sensitive.

TABLE 5

Serological performance of fusion CFP10/ESAT6 vs. single antigens in the lateral-flow format with primate samples.*

| Animal ID# | CFP10/ESAT6 | ESAT6 | CFP10 | ESAT6 + CFP10 |
|---|---|---|---|---|
| 304-14 | +++ | + | − | + |
| 653-17 | +++ | − | − | − |
| 855-6 | ++ | − | + | − |
| 729-7 | ++++ | +++ | + | +++ |
| 283-14 | + | + | − | ++ |
| 056-14 | + | − | − | − |
| 590-17 | ++ | − | + | − |
| 814-8 | ++ | − | + | − |
| 847-15 | + | − | − | − |
| 867-10 | ++ | − | − | − |

*Rhesus macaques were experimentally infected with *M. tuberculosis* and sera were collected 6 to 17 weeks later. Tests used 5 μl of sample and were read at 15 minutes. Results are shown as negative (−) or positive (+, weak; ++, moderate; +++, strong; or ++++, very strong).

TABLE 6

Diagnostic specificity of Latex Lateral Flow Test

| Species | Site/Origin | Number of negative results | Specificity (%) |
|---|---|---|---|
| Rhesus | Tulane National Primate Center | 28/30 | 93.3 |
| | University of South Alabama | 5/5 | 100.0 |
| | Rutgers University | 5/5 | 100.0 |
| | Biomedical Primate Research Center (Netherlands) | 15/15 | 100.0 |
| Cynomolgus | Biomedical Primate Research Center (Netherlands) | 6/6 | 100.0 |
| African green | Behaviour Science Foundation (St. Kitts) | 84/84 | 100.0 |
| Squirrel | University of South Alabama | 12/12 | 100.0 |
| Total | | 155/157 | 98.7 |

TABLE 7

Diagnostic sensitivity of Latex Lateral Flow Test

| Species | Site/Origin | Infection | Number of positive results | Sensitivity (%) |
|---|---|---|---|---|
| Rhesus | Tulane National Primate Center | Experimental, *M. tuberculosis,* H37Rv/Erdman | 8/9 | 88.9 |
| | University of South Alabama | Experimental, *M. tuberculosis,* Erdman | 4/5 | 80.0 |
| | Biomedical Primate Research Center (Netherlands) | Experimental, *M. tuberculosis,* Erdman/Beijing | 7/9 | 77.8 |
| | Stanford University | Natural *M. bovis* outbreak | 7/7 | 100.0 |
| Cynomolgus | Biomedical Primate Research Center (Netherlands) | Experimental, *M. tuberculosis,* Erdman | 3/3 | 100.0 |
| | Stanford University | Natural *M. bovis* outbreak | 16/18 | 88.9 |
| Total | | | 45/51 | 88.2 |

TABLE 8

TST, PRIMAGAM and Latex Lateral Flow Test in Stanford *M. bovis* outbreak

| Test | Sensitivity (%) |
|---|---|
| TST | 85 (23/27) |
| PRIMAGAM | 68 (17/25) |
| Latex Lateral Flow Test | 92 (23/25) |

What is claimed is:

1. A method for detecting antibodies to one or more mycobacterial antigens in a sample from a non-human primate, comprising:

obtaining the sample from the non-human primate;

contacting the sample with a first composition comprising an antigen-particle conjugate comprising multiple mycobacterial antigens conjugated to a particle, wherein contacting the sample with the first composition permits the binding of antibodies to one or more of the mycobacterial antigens and formation of an antibody-antigen-particle complex;

contacting the sample with a second composition comprising multiple mycobacterial antigens immobilized at one or more locations on a solid support, permitting binding of the antibody-antigen-particle to one or more immobilized antigens of the second composition;

and detecting the formation of the bound antibody-antigen-particle complex;

wherein each antigen present in the first composition is present in the second composition.

2. The method of claim 1, wherein at least two of the mycobacterial antigens of the first composition, the second composition, or both the first and second composition are combined in a polyfusion protein.

3. The method of claim 1, wherein the mycobacterial antigens of the first and second compositions are isolated directly from a one or more mycobacteria selected from the group consisting of *Mycobacterium tuberculosis, Mycobacterium bovis, Mycobacterium avium-intracellulare, Mycobacterium kansasii, Mycobacterium fortuitum, Mycobacterium chelonae, Mycobacterium leprae, Mycobacterium africanum*, and *Mycobacterium microti* or synthesized by chemical or biological means.

4. The method of claim 1, wherein the mycobacterial antigens of the compositions comprise amino acid sequences selected from ESAT-6, CFP-10, Mo-29, Mtb8, Arc1, 38 KDa, Mtb48, MPB70, MPT70, MPB83, MPT83, MPT63, MPB63, MPB64 or MPT64.

5. The method of claim 2, wherein the mycobacterial antigens of the compositions comprise MPB83, CFP10/ESAT-6 and TBF10.

6. The method of claim 1, wherein the mycobacterial antigens of the second composition comprise amino acid sequences selected from ESAT-6, CFP10, Mo-29, Mtb8, Arc1, 38 KDa, Mtb48, MPB70, MPT70, MPB83, MPT83, MPT63, MPB63, MPB64 or MPT64.

7. The method of claim 2, wherein the mycobacterial antigens of the second composition comprise MPB83, CFP10/ESAT-6 and TBF10.

8. The method of claim 1, wherein the particles are latex particles.

9. The method of claim 1, wherein the particles are colloidal gold particles.

10. The method of claim 1, further comprising the steps of: contacting the sample with a third composition comprising one or more molecules capable of non-specifically binding non-human primate antibodies, wherein the third composition is immobilized on a solid support, permitting binding of antigen-particle conjugates not bound by the second composition on the solid support; and detecting the antigen-particle conjugates on the solid support.

11. The method of claim 10, wherein the third composition comprises one or more of Protein A, Protein G, Protein AG, Protein L, or non-human primate anti-IgG.

12. The method of claim 1, wherein the step of contacting the sample with the conjugate is performed in solution.

13. The method of claim 1, wherein the conjugate is located on the solid support.

14. The method of claim 1, wherein the solid support is a membrane.

15. The method of claim 14, wherein the membrane is a lateral flow membrane.

16. The method of claim 1, wherein the antibodies to one or more mycobacterial antigens comprise one or more of IgG or IgM.

17. The method of claim 1, wherein the test sample comprises serum, plasma, blood, urine, or saliva, or a mixture of two or more of serum, plasma, blood, urine, or saliva.

18. The method of claim 1, wherein the mycobacterial antigens of the first or second composition are selected by MAPIA screening, comprising:
immobilizing mycobacterial antigens onto a membrane;
contacting the membrane with a serum of the non-human primate, comprising the antibodies to the one or more of the mycobacterial antigens; and detecting binding of the antibodies to one or more of the mycobacterial antigens.

19. A method for detecting antibodies to one or more mycobacterial antigens in a sample from a non-human primate, comprising:
obtaining the sample from the non-human primate;
contacting the sample with a first composition comprising particles conjugated to one or more molecules capable of non-specifically binding non-human primate antibodies, permitting formation of a non-specific antibody-conjugate complex;
after the step of contacting the sample with the conjugate, contacting the sample with a second composition comprising a mixture of mycobacterial antigens immobilized on a solid support capable of binding the antibody-conjugate complex and permitting formation of an immobilized mycobacterial antigen-antibody-conjugate complex;
after the step of contacting the sample with the second composition, contacting the sample with a third composition comprising one or more molecules capable of non-specifically binding non-human primate antibodies, wherein the third composition is immobilized on the solid support, permitting trapping of the non-specific antibody-conjugate complex that did not bind to the second composition;
detecting the formation of the immobilized antigen-antibody-conjugate complex; and
detecting the trapped non-specific antibody-conjugate complex on the solid support.

20. The method of claim 19, wherein two or more of the mycobacterial antigens of the second composition are combined in a polyfusion protein.

21. The method of claim 19, wherein the mycobacterial antigens are isolated directly from a one or more mycobacteria selected from the group consisting of *Mycobacterium tuberculosis, Mycobacterium bovis, Mycobacterium aviumintracellulare, Mycobacterium kansasii, Mycobacterium fortuitum, Mycobacterium chelonae, Mycobacterium leprae, Mycobacterium africanum*, and *Mycobacterium microti* or synthesized by chemical or biological means.

22. The method of claim 19, wherein the mycobacterial antigens comprise one or more amino acid sequences selected from ESAT-6, CFP-10, Mo-29, Mtb8, Arc 1, 38 KDa, Mtb48, MPB70, MPT70, MPB83, MPT83, MPT63, MPB63, MPB64 or MPT64.

23. The method of claim 19, wherein the mycobacterial antigens comprise MPB83, CFP10/ESAT-6 and TBF10.

24. The method of claim 19, wherein the particles are latex particles.

25. The method of claim 19, wherein the particles are colloidal gold particles.

26. The method of claim 19, wherein the first composition comprises one or more of Protein A, Protein G, Protein AG, Protein L, or non-human primate anti-IgG.

27. The method of claim 19, wherein the third composition comprises one of more of Protein A, Protein 0, Protein AG, Protein L, or non-human primate anti-IgG.

28. The method of claim 19, wherein the step of contacting the sample with the conjugate is performed in solution.

29. The method of claim 19, wherein the conjugate is located on the solid support.

30. The method of claim 19, wherein the solid support is a membrane.

31. The method of claim 19, wherein the solid support is a lateral flow membrane.

32. The method of claim 19, wherein the antibodies are IgG or IgM.

33. The method of claim 19, wherein the test sample comprises serum, plasma, blood, urine, or saliva, or a mixture of two or more of serum, plasma, blood, urine, or saliva.

34. The method of claim 19, wherein one or more of the mycobacterial antigens of the second composition are selected by MAPIA screening, comprising: immobilizing mycobacterial antigens onto a membrane; contacting the membrane with a serum of the non-human primate, comprising the antibodies to the mycobacterial antigens; and detecting binding of the antibodies to one or more of the mycobacterial antigens.

35. A composition for detecting antibodies to one or more mycobacterial antigens in nonhuman primates, comprising a mixture of mycobacterial antigens immobilized on a solid support, wherein at least two of the mycobacterial antigens are combined in a polyfusion protein which binds to non-human primate antibodies, said polyfusion protein selected from the group consisting of CFP10/ESAT-6, TBF10, and Arc1/MPB83.

36. The composition of claim 35, wherein the mycobacterial antigens are isolated directly from a mycobacterial species selected from the group consisting of *Mycobacterium tuberculosis, Mycobacterium bovis, Mycobacterium avium-intracellulare, Mycobacterium kansasii, Mycobacterium fortuitum, Mycobacterium chelonae, Mycobacterium leprae, Mycobacterium africanum*, and *Mycobacterium microti* or synthesized by chemical or biological means.

37. The composition of claim 35, wherein the mycobacterial antigens comprise one or more amino acid sequences selected from ESAT-6, CFP-10, Mo-29, Mtb8, Arc1, 38 KDa, Mtb48, MPB70, MPT70, MPB83, MPT83, MPT63, MPB63, MPB64 or MPT64.

38. The composition of claim 35, wherein the solid support is a lateral flow membrane.

39. The composition of claim 35, wherein the solid support is a nylon, polyvinyl difluoride, or nitrocellulose membrane.

40. A composition for detecting antibodies to one or more mycobacterial antigens in nonhuman primates comprising a plurality of particles, and a mixture of mycobacterial antigens selected to bind to nonhuman primate antibodies and comprising at least two of amino acid sequences selected from ESAT-6, CFP-10, Mo-29, MPB70, MPT70, MPB83, MPT83, MPT63, MPB63, MPB64 and MPT64, each individual antigen of said mixture of mycobacterial antigens conjugated to at least one of said plurality of particles, and each particle of said plurality of particles conjugated to at least one individual antigen.

41. The composition of claim 40, wherein the mycobacterial antigens are isolated directly from mycobacterial species selected from the group consisting of *Mycobacterium tuberculosis, Mycobacterium bovis, Mycobacterium avium-intracellulare, Mycobacterium kansasii, Mycobacterium fortuitum, Mycobacterium chelonae, Mycobacterium leprae, Mycobacterium africanum*, and *Mycobacterium microti*, or synthesized by chemical or biological means.

42. The composition of claim 40, wherein the plurality of particles are latex particles.

43. The composition of claim 40, wherein the plurality of particles are colloidal gold particles.

* * * * *